United States Patent
Moulton

(10) Patent No.: US 6,472,379 B1
(45) Date of Patent: Oct. 29, 2002

(54) ANGIOGENESIS INHIBITION

(75) Inventor: Steven Moulton, Weston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/525,402

(22) Filed: Mar. 15, 2000

Related U.S. Application Data
(60) Provisional application No. 60/124,703, filed on Mar. 15, 1999.

(51) Int. Cl.7 .......................... A61K 31/715; A61K 9/70
(52) U.S. Cl. .............................. 514/54; 514/55; 514/56; 514/57; 514/58; 514/59; 424/447; 424/488
(58) Field of Search ....................... 514/54–59; 424/447, 424/488

(56) References Cited

U.S. PATENT DOCUMENTS

| | | | |
|---|---|---|---|
| 4,582,865 A | 4/1986 | Balazs et al. | 524/29 |
| 4,771,042 A | 9/1988 | Braughler et al. | 514/171 |
| 4,937,270 A | 6/1990 | Hamilton et al. | 514/777 |
| 5,001,116 A | 3/1991 | Folkman et al. | 514/56 |
| 5,017,229 A | 5/1991 | Burns et al. | 106/162 |
| 5,356,883 A * | 10/1994 | Kuo et al. | 514/54 |
| 5,690,961 A * | 11/1997 | Nguyen | 424/488 |
| 5,847,002 A | 12/1998 | Willoughby et al. | 514/561 |
| 5,866,554 A | 2/1999 | Shalaby et al. | 514/54 |
| 5,902,795 A | 5/1999 | Toole et al. | 514/54 |
| 5,994,341 A | 11/1999 | Hunter et al. | 514/210 |
| 6,001,356 A | 12/1999 | Mikecz et al. | 424/144.1 |
| 6,022,866 A | 2/2000 | Falk et al. | 514/54 |

FOREIGN PATENT DOCUMENTS

| | | | |
|---|---|---|---|
| EP | 0507604 | * 4/1992 | |
| WO | WO 92/00105 | 1/1992 | A61K/47/26 |
| WO | 0 507 604 A2 | 10/1992 | A61K/31/725 |
| WO | WO 92/20349 | 11/1992 | A61K/31/725 |
| WO | WO 96/05845 | 2/1996 | A61K/31/725 |
| WO | WO 97/40841 | 11/1997 | A61K/31/715 |

OTHER PUBLICATIONS

Caplus abstract 1997:158939.*
Derwent abstract of JP100017, Jan. 1986.*
Danishefsky, I. and Siekovic, E., "Conversion of Carboxyl Groups of Mucopolysaccharides into Amides of Amino Acid Esters," *Carbohydrate Research*, 16; 199–205 (1971).
Bigatti, G., et al., "*Experimental model for neoangiogenesis in adhesion formation*," Human Reproduction, 10, 2290–2294 (1995).
Dhed et al., "Early–Response Gene Signalling is Induced by Angiogenic Oligosaccharides of Hyaluronan in Endothelial Cells, Inhibition by Non–Angiogenic, High–Molecular-Weight Hyaluronan," *Int'l J of Cancer*, vol. 71, 1997, pp. 251–256.

* cited by examiner

Primary Examiner—James O. Wilson
Assistant Examiner—Leigh C. Maier
(74) Attorney, Agent, or Firm—Ropes & Gray

(57) ABSTRACT

Angiogenesis is inhibited by the local administration of a pharmaceutical preparation formed from the reaction of hyaluronic acid, carboxymethylcellulose and a carbodiimide. The preparation, which can be in the form of a film or a gel, is advantageously applied directly to the site of a tumor, such as a cancerous tumor, used in conjunction with other chemotherapeutic techniques, or used to treat a chronic inflammatory condition, such as rheumatoid arthritis, endometriosis, arteriosclerosis, intimal hyperplasia, proliferative retinopathy, and the like.

3 Claims, 3 Drawing Sheets

Day 10, P = 0.4

Day 15, P <.0001

Day 35, P = .0002

Day 15, P < .0001

Day 35, P = .0001

Day 10, P = .02

Day 15, P = .09

Day 35, P = 0.15

ANGIOGENESIS INHIBITION

CROSS-REFERENCE TO RELATED APPLICATIONS

This application claims the benefit of U.S. Provisional Application No. 60/124,703 filed Mar. 15, 1999, the contents of which are incorporated herein by reference in their entirety.

BACKGROUND OF THE INVENTION

This invention relates to methods for inhibiting angiogenesis in a mammal by the local administration of an activated hyaluronic acid composition to the site where the anti-angiogenesis effect is desired. The anti-angiogenesis method of this invention can be used to control or inhibit solid tumor growth in cancer patients, to modulate wound healing, and to prevent or reduce inflammation.

Vasculogenesis is a necessary process in the establishment of embryonic tissue whereby endothelial cells are born from progenitor cell types. In contrast, angiogenesis is a process wherein new capillaries sprout from existing vessels. Thus, angiogenesis is necessary for the establishment and development of tumor tissue, as well as the control of certain inflammatory conditions. Angiogenesis is also known to play an integral role in wound healing by allowing tissue generation and remodeling. The inhibition of angiogenesis can be a useful tool for the control of wound healing, inflammation and solid tumor growth.

Angiogenesis-dependent diseases are those diseases which require or induce vascular growth. Such diseases represent a significant portion of all diseases for which medical treatment is sought, and include cancers and inflammatory arthritis.

Standard approaches for the treatment and management of cancer involve the use of surgical procedures to excise the tumor, followed by the use of chemotherapeutic drugs and/or radiation treatment to prevent a reoccurrence of the cancer. The chemotherapeutic drugs, such as cisplatin and methotrexate, are typically introduced directly into the patient's blood stream and carried to the site of the tumor. There is now evidence, however, that tumors actually compress their blood supply, making it difficult for the drug to reach the target cancer cells. In order to reach the cancer cells, the drugs must cross the blood-vessel wall and the interstitial spaces within the tumor. An alternative approach is to develop drugs which will inhibit the growth of blood vessels within the tumor.

U.S. Pat. No. 4,771,042 discloses steroid compositions which are useful for inhibiting angiogenesis. These compositions are administered intramuscularly, intravenously or orally, and are useful for treating various traumas, cancer and infertility.

U.S. Pat. No. 5,001,116 describes the inhibition of angiogenesis by the co-administration of heparin and steroids. The patent discloses that neither the steroids nor heparin alone have any anti-angiogenic activity, and it is the combination of the two which is unexpectedly effective for this purpose. The routes of administration are parenteral or oral, and the compositions are disclosed as being particularly useful for tumor regression or to prevent metastasis.

Hyaluronic acid ("HA") is a naturally occurring mucopolysaccharide found, for example, in synovial fluid, in vitreous humor, in blood vessel walls and the umbilical cord, and in other connective tissues. The polysaccharide consists of alternating N-acetyl-D-glucosamine and D-glucuronic acid residues joined by alternating β1-3 glucuronidic and β1-4 glucosaminidic bonds, so that the repeating unit is -(1→4)-β-D-GlcA-(1→3)-β-D-GlcNAc-. In water, hyaluronic acid dissolves to form a highly viscous fluid. The molecular weight of hyaluronic acid isolated from natural sources generally falls within the range of $5 \times 10^4$ up to $1 \times 10^7$ daltons.

Hyaluronic acid, in chemically modified ("derivatized") or crosslinked form, is useful as a surgical aid to prevent adhesions or accretions of body tissues during the post-operative period. The derivatized or crosslinked HA gel or film is injected or inserted into the locus between the tissues that are to be kept separate to inhibit their mutual adhesion. Chemically modified or crosslinked HA can also be useful for controlled release drug delivery. See U.S. Pat. Nos. 4,937,270 and 5,017,229 which disclose derivatized versions of HA, or HA in combination with other polyanionic polysaccharides such as carboxymethylcellulose, which can be prepared by reacting the HA with a carbodiimide. U.S. Pat. No. 4,582,865, and pending U.S. application Ser. No. 09/503,544, filed Feb. 14, 2000, each describe the reaction of hyaluronic acid with divinyl sulfone, and the use of these products in medical applications.

A derivatized version of HA and carboxymethylcellulose ("CMC"), in combination, is available commercially as Seprafilm™ membranes and films from the Genzyme Corporation. CMC is an anionic polysaccharide and a derivatized form of cellulose in which the glucosidic hydroxyl groups have been carboxymethylated, thereby rendering the polymer water soluble. This derivative of HA and CMC can be prepared by mixing HA with CMC and an activating agent to form a water insoluble precipitate. The precipitate is cast into a thin film membrane, which can be implanted into the peritoneal cavity or other sites to prevent the formation of post-operative adhesions.

I. Danishefsky et al., *Carbohydrate Res.*, Vol. 16, pages 199–205, 1971, describe modifying a mucopolysaccharide by converting the carboxyl groups of the mucopolysaccharide into substituted amides by reacting the mucopolysaccharide with an amino acid ester in the presence of 1-ethyl-3-(3-dimethylaminopropyl)carbodiimide hydrochloride ("EDC") in aqueous solution. Danishefsky et al. react glycine methyl ester with a variety of polysaccharides, including HA. The resulting products are water soluble; that is, they rapidly disperse in water or in an aqueous environment such as is encountered between body tissues.

U.S. Pat. No. 5,847,002 describes a method for inhibiting, controlling or regressing angiogenesis by administering to a subject a non-steroidal anti-inflammatory agent ("NSAID") and hyaluronic acid ("HA"). The function of the NSAID is to decrease the production of inflammatory mediators, many of which are pro-angiogenic, thereby inhibiting granuloma formation. The patent states that the NSAID and HA act synergistically as an angiostatic agent.

U.S. Pat. No. 5,902,795 discloses the use of hyaluronan oligosaccharides and antibodies to hyaluronan binding proteins to treat tumors or other diseases which can be linked to angiogenesis. The compositions of this patent block the hyaluronan binding protein on the cell surface during tumor cell and endothelial cell migration, and during capillary-like tubule formation.

U.S. Pat. No. 6,022,866 describes the use of solutions of hyaluronic acid to prevent arterial restinosis. The hyaluronic acid solution is administered to a patient to prevent the narrowing of the tubular walls of an artery after being traumatized, such as the narrowing which can occur following a balloon angioplasty procedure.

It will be appreciated that there is a need for an improved anti-angiogenesis formulation and therapeutic treatments which use such formulations.

SUMMARY OF THE INVENTION

In general terms, the present invention features a method for inhibiting angiogenesis in a mammal by the local administration of an activated hyaluronic acid composition to the site where the anti-angiogenesis result is desired. The anti-angiogenesis method of this invention can be used to control or inhibit solid tumor growth in cancer patients, to modulate wound healing, and to prevent or reduce inflammation and inflammatory diseases.

In one aspect, the activated polyanionic polysaccharide is formed by reacting the polyanionic polysaccharide with a carbodiimide in an aqueous medium under suitable reaction conditions. The preferred pH for carrying out the reaction is 3.5 to 8.0. The preferred concentration for the polyanionic polysaccharide is from about 0.005 to 0.1M, more preferably from about 0.01 to 0.02M. The molar ratio of the polyanionic polysaccharide to activating agent is preferably at least 1:1, and more preferably about 1:4. The preferred carbodiimide is 1-ethyl-3-(3-dimethylaminopropyl) carbodiimide or 1-ethyl-3-(3-dimethylaminopropyl) carbodiimide methiodide.

In a further aspect, the crosslinked polyanionic polysaccharide compositions are prepared by reacting the polyanionic polysaccharide with a suitable crosslinking agent, such as divinyl sulfone, in a solvent under suitable reaction conditions.

In another aspect, the anti-angiogenesis compositions of this invention are used in a therapeutic method for the treatment of solid cancerous tumors and surrounding tissue. The compositions of this invention can be used alone, or in combination with other anti-angiogenic compositions, such as steroids, which can be administered to the site of the cancerous tumor. The pharmaceutical preparations can also include other pharmaceutically active substances dispersed throughout, making the preparations useful as drug delivery vehicles. Suitable pharmaceutically active substances include proteins, such as growth factors, soluble receptors and enzymes, drugs, antibodies, biopolymers, and biologically compatible synthetic polymers.

In a further aspect, this invention encompasses a method for the treatment of non-tumorigenic, angiogenesis-dependent diseases by the administration of the present compositions to the site of the inflammation to inhibit the formation of new blood vessels. Preferred angiogenesis-dependent diseases which may be treated by the compositions of this invention include, for instance, inflammatory arthritis, such as rheumatoid arthritis.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the preferred methods and materials are now described. All publications mentioned hereunder, including published patent applications, and issued or granted patents, are incorporated by reference in their entirety. Unless mentioned otherwise, the techniques employed or contemplated herein are standard methodologies well known to one of ordinary skill in the art. The materials, methods and examples are illustrative only and not intended to be limiting.

Other features and advantages of the invention will be apparent from the following description of the preferred embodiments, and from the claims.

DETAILED DESCRIPTION

Figure 1:
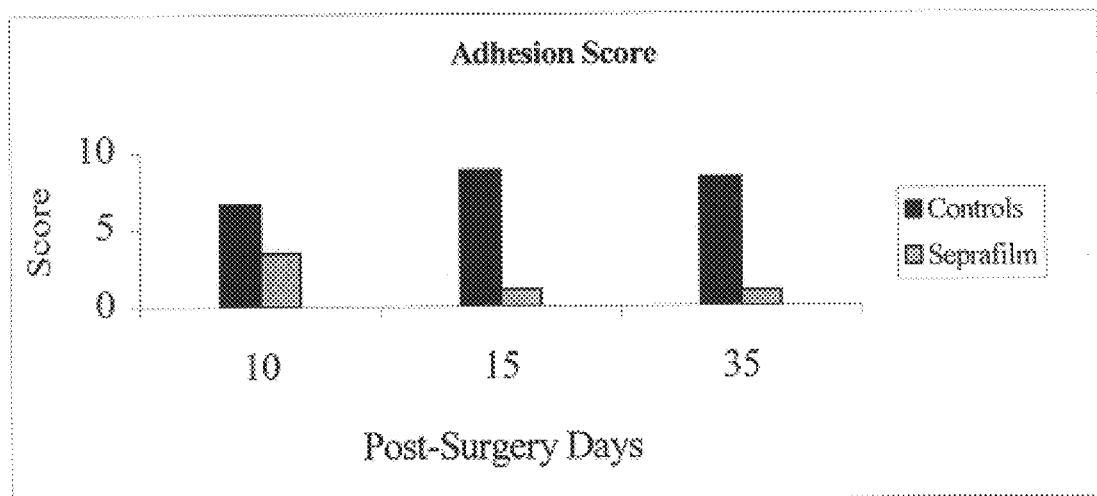
FIG. 1 is a bar graph illustrating the adhesion scores for Seprafilm treated and control animals at 10, 15 and 35 days following surgery.

The pharmaceutical compositions of this invention are prepared by reacting a polyanionic polysaccharide, such as hyaluronic acid or carboxymethylcellulose, with a suitable activating agent, such as a carbodiimide. Preparations of this type are well known in the art, and are disclosed, for instance, in U.S. Pat. No. 5,017,229, the disclosure of which is incorporated by reference herein.

As used herein, and unless otherwise indicated, the terms "HA" and "hyaluronic acid" denote hyaluronic acid and any of its hyaluronate salts, including, for example, sodium hyaluronate (the sodium salt), potassium hyaluronate, magnesium hyaluronate, and calcium hyaluronate. The term "polyanionic polysaccharide" means hyaluronic acid (HA), carboxymethylcellulose ("CMC"), carboxymethylamylose ("CMA"), chondroitin sulfate, dermatin sulfate, heparin, and heparin sulfate.

The term "CMC and "carboxymethylcellulose" refer to the carboxymethyl derivatized form of cellulose in which the glucosidic hydroxyl groups have been carboxymethylated to render the polymer water soluble, as well as substituted and modified versions of the molecule.

"Angiogenesis", as used herein, refers to the formation of new blood vessels from pre-existing blood vessels. Angiogenesis is turned on and off by the upregulated expression of angiogenic growth factors or by angiogenesis inhibitors. Angiogenesis is thought to play an integral role in wound healing since tissue generation and remodeling can only occur when accompanied by blood vessel formation.

"Local administration" means contacting the pharmaceutical preparation with tissue surfaces in the immediate proximity to the tumor in the body where the anti-angiogenesis effect is desired. The preparation may be in the form of a film or gel. The film or gel may be inserted into the site of the trauma or cancer by an attending physician. A convenient method for local administration, particularly in the case of a gel formulation, is the use of a minimally invasive surgical procedure for installing the product.

A "gel" is a substance having a consistency which varies from a solid or semi-solid to a liquid. A "film" is a thin flexible sheet or membrane which can readily be folded and manipulated to conform to a desired shape. A film can be a gel product which has substantially all of the moisture removed therefrom.

An "activating agent" is a substance that, in an aqueous mixture including hyaluronic acid, renders the carboxyl groups on the hyaluronic acid vulnerable to nucleophilic attack.

An "acyl derivative," as that term may be used herein, is a compound produced by the displacement of the hydroxyl group bound to the acyl carbon atom of a carboxylic acid moiety by either the reaction of the hydroxyl group with a nucleophilic group of another compound, or by the rearrangement of the O-acylisourea formed by reaction of the hydroxyl group with a carbodiimide. Examples of acyl derivatives include acylureas, acylisoureas, amides, thioesters, and phenolates.

A "mammal" shall mean a human or non-human mammal, including but not limited to, a dog, cat, horse, cow, pig, sheep, goat, chicken, primate, rat, and mouse.

The activated polyanionic polysaccharide of this invention can be prepared by treating a polyanionic polysaccharide with a suitable carbodiimide in the presence or absence of a nucleophile. Preferably, the polyanionic polysaccharide is hyaluronic acid. The resulting product may be water soluble or water insoluble, depending on the reaction conditions and the relative proportions of ingredients in the reaction mixture. The reaction of the carbodiimide with the carboxyl group of the hyaluronic acid proceeds through the addition of the free carboxylate to one of the double bonds of the diimide to give the O-acylisourea derivatives of the hyaluronic acid and the carbodiimide. In the presence of a nucleophile, such as a primary amine, the amide derivative of the hyaluronic acid forms as well as the unimolecular O→N rearrangement of the O-acylisourea derivatives to give the more stable N-acylurea derivatives of the hyaluronic acid and the carbodiimide. In the absence of a nucleophile, the intramolecular rearrangement from the O-acylisourea derivatives to the N-acylurea derivatives is the predominant reaction.

The hyaluronic acid, or a salt of hyaluronic acid, such as sodium hyaluronate, is dissolved in water to make an aqueous mixture. HA from any of a variety of sources can be used. As is well known to those skilled in the art, HA can be extracted from animal tissues or harvested as a product of bacterial fermentation. Hyaluronic acid can be produced in commercial quantities by bioprocess technology, as described for example in PCT Publication No. WO 86/04355. Preferably the concentration of HA in this first aqueous mixture is in the range between 0.05% to 2.0% weight/weight ("w/w"), and more preferably 0.1% to 1%. Subsequent reactions are slower and less effective at significantly lower concentrations, while significantly higher concentrations are difficult to handle owing to their high viscosity. The aqueous HA mixture should be acidic, preferably having a pH between pH 3.5 and pH 8.0. At lower pH values the preferred activating agent, EDC, is unstable, and at higher values the reaction rate is diminished. Preferably hydrochloric acid is added to adjust the pH, although other known acids can be used.

Once the pH of the aqueous HA mixture has been adjusted, a carbodiimide is admixed with the HA. Preferred carbodiimides include EDC (in some references this substance is termed 1-(3-dimethylaminopropyl)-3-ethyl-carbodiimide or "DEC") or ETC (1-ethyl-3-(3-dimethylaminopropyl)carbodiimide methiodide).

The mode of addition of the reagents is not critical, but the ratio of the carbodiimide to HA is important. Lower ratios typically form weaker, less insoluble products, while higher ratios typically result in stronger, more insoluble products. It is generally advantageous to have a more insoluble product since the substrate can be thoroughly washed with water without appreciable deterioration.

The pharmaceutical preparations of this invention are preferably administered locally to the site of the trauma, inflammation or cancer. They can be used in conjunction with other therapies, such as chemotherapy for treating solid cancerous tumors or tissue, and they can be used in combination with other anti-angiogenesis products and compositions.

For the treatment of cancer, the compositions of this invention can be used to coat an area prior to or after the removal of a solid tumor. The compositions may also be delivered by endoscopic procedures to coat the tumor and/or the surrounding area, or to inhibit angiogenesis in the desired area. The compositions of this invention can also be used to treat tumor excision sites. The types of tumors which may be treated in this manner include colon tumors, breast tumors, brain tumors, and hepatic tumors, among others.

The compositions can also be used to treat inflammatory arthritis, such as rheumatoid arthritis, by administering the compositions to a joint, for example. Other angiogenesis-dependent diseases which may be treated in accordance with the methods of this invention include psoriasis, purogenic granuloma, scleroderma, trachoma, endometriosis, arteriosclerosis, intimal hyperplasia, proliferative retinopathy, and the like.

Treatment methods which can be advantageously used in the practice of this invention include those disclosed in U.S. Pat. No. 5,994,341, the disclosure of which is incorporated by reference herein in its entirety.

The present invention provides pharmaceutical compositions, for medical use, which in some aspects comprise the anti-angiogenesis compositions of the invention together with one or more pharmaceutically acceptable carriers and optionally other therapeutic ingredients. Thus the invention also relates to anti-angiogenesis pharmaceutical compositions in combination with an anti-infectious agent such as an antibacterial or anti-viral agent, an anti-inflammatory agent, or other therapeutic agent and a pharmaceutically acceptable carrier. The pharmaceutical compositions useful in the invention may be delivered separately with the other therapeutic agent or in the form of therapeutic cocktails. A therapeutic cocktail is a mixture of any pharmaceutical composition of the invention and another therapeutic agent. In this embodiment, a common administration vehicle could contain both the pharmaceutical composition and the other therapeutic agent. Alternatively, the other therapeutic agent can be separately dosed.

The precise amounts of the therapeutic agent used in combination with the pharmaceutical compositions of the invention will depend upon a variety of factors, including the pharmaceutical composition selected, the dose and dose-timing selected, the mode of administration, the nature of any surgical or medical procedure contemplated and the characteristics of the subject. Where local administration is carried out, it will be understood that very small amounts may be required (nanograms and possibly picograms). The precise amounts selected can be determined without undue experimentation, particularly since a threshold amount will be any amount which will favorably enhance the desired response. Thus, it is believed that picogram to milligram amounts are possible, depending upon the mode of delivery, but that nanogram to microgram amounts are likely to be most useful.

Multiple doses of the pharmaceutical compositions of the invention are contemplated. For instance, when being administered in conjunction with a surgical procedure the compounds of the invention can be administered in multiple doses over a three week period preceding surgery, over a two week period preceding surgery, over a one week period preceding surgery, over a one day period preceding surgery, etc. Further doses may be administered post surgery as well. Any regimen that prevents an inflammatory response may be used, although optimum doses and dosing regimens are those that would not only inhibit the development of cancer or the inflammatory disease, but also would prevent the reoccurrence of cancer or the inflammatory disease. Desired time intervals for delivery of multiple doses of a particular pharmaceutical composition can be determined by one of ordinary skill in the art employing no more than routine experimentation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1–2% w/v); citric acid and a salt (1–3% w/v); boric acid and a salt (0.5–2.5% w/v); and phosphoric acid and a salt (0.8–2% w/v). Suitable preservatives include benzalkonium chloride (0.003–0.03% w/v); chlorobutanol (0.3–0.9% w/v); parabens (0.01–0.25% w/v) and thimerosal (0.004–0.02% w/v).

The pharmaceutical compositions of the invention contain an effective amount of a pharmaceutical composition optionally included in a pharmaceutically acceptable carrier. The term "pharmaceutically acceptable carrier" means one or more compatible solid or liquid filler, dilutants or encapsulating substances which are suitable for administration to a human or other mammals. The term "carrier" denotes an organic or inorganic ingredient, natural or synthetic, with which the active ingredient is combined to facilitate the application. The components of the pharmaceutical compositions also are capable of being commingled with the pharmaceutical compositions of the present invention, and with each other, in a manner such that there is no interaction which would substantially impair the desired pharmaceutical efficiency.

The pharmaceutical compositions useful in the invention may be delivered in mixtures of more than one pharmaceutical composition. A mixture may consist of several pharmaceutical compositions.

A variety of administration routes are available. The particular mode selected will depend, of course, upon the particular pharmaceutical composition selected, the particular condition being treated and the dosage required for therapeutic efficacy. The methods of this invention, generally speaking, may be practiced using any mode of administration that is medically acceptable, meaning any mode that produces effective levels of the anti-angiogenesis response without causing clinically unacceptable adverse effects. Preferred modes of administration include, e.g., deposition, implantation, and topical administration.

In certain preferred embodiments of the invention, the administration can be designed so as to result in sequential exposure of the pharmaceutical composition over some period of time, e.g., hours, days, weeks, months or years. This can be accomplished by repeated administrations of the pharmaceutical composition, by one of the methods described above, or alternatively, by a sustained-release delivery system in which the pharmaceutical composition is delivered to the subject for a prolonged period without repeated administrations. By sustained-release delivery system, it is meant that total release of the pharmaceutical composition does not occur immediately upon administration, but rather is delayed for some period of time.

The compositions may conveniently be presented in unit dosage form and may be prepared by any of the methods well known in the art of pharmacy. All methods include the step of bringing the pharmaceutical composition into association with a carrier which constitutes one or more accessory ingredients. In general, the compositions are prepared by uniformly and intimately bringing the pharmaceutical composition into association with a liquid carrier, a finely divided solid carrier, or both, and then, if necessary, shaping the product.

The pharmaceutical compositions are administered to the mammal in a therapeutically-effective amount. By therapeutically-effective amount it is meant that amount which is capable of at least partially preventing, reversing, reducing, decreasing, ameliorating, or otherwise suppressing the inflammatory response being treated. A therapeutically-effective amount can be determined on an individual basis and will be based, at least in part, on consideration of the species of mammal, the mammal's age, sex, size, and health; the type of pharmaceutical composition used, the type of delivery system used; the time of administration relative to the severity of the disease; and whether a single, multiple, or controlled-release dose regimen is employed. A therapeutically-effective amount can be determined by one of ordinary skill in the art employing such factors and using no more than routine experimentation.

In some embodiments, the concentration of the pharmaceutical composition if administered systemically is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. Preferably, the concentration of the pharmaceutical composition, if applied topically, is about 0.1 mg to about 500 mg/gm of gels or other base, more preferably about 1.0 mg to about 100 mg/gm of base, and most preferably, about 30 mg to about 70 mg/gm of base. The specific concentration partially depends upon the particular pharmaceutical composition used, as some are more effective than others. The dosage concentration of the pharmaceutical composition actually administered is dependent at least in part upon the particular disorder being treated, the final concentration of pharmaceutical composition that is desired at the site of action, the method of administration, the efficacy of the particular pharmaceutical composition, the longevity of the particular pharmaceutical composition, and the timing of administration relative to the severity of the disease. Preferably, the dosage form is such that it does not substantially deleteriously effect the mammal. The dosage can be determined by one of ordinary skill in the art employing such factors and using no more than routine experimentation.

Without wishing to be bound by any particular theory or mechanism of action, it is believed that the early reduction in vessel growth due to the anti-angiogenic effect of the instant preparations also contributes to long term adhesion reduction. Intraabdominal adhesions begin as fibrinous adhesions, which are transient and may be completely lysed within 72 hours if the fibrinolytic system is active and there is no underlying tissue ischemia. If the fibrinolytic system is depressed, foreign material remains or there is persistent tissue ischemia, the fibrinous adhesions persist. They are thought to play a principal role in peritoneal or mesothelial wound healing by providing a scaffolding for the ingrowth of new blood vessels, i.e. angiogenesis, the delivery of cellular elements, and the subsequent proliferation of fibroblasts. Wound healing in this setting is characterized by a variety of redundant, overlapping and sequential processes involving a wide variety of cytokines, chemoattractants, mitogens, growth factors, and cellular mediators. During this process, the cells in the developing adhesion differentiate and synthesize extracellular matrix to form a fibrous adhesion. Accordingly, these fibrous adhesions are precursors in the development of mature intraabdominal adhesions.

It is also believed that angiogenesis plays a significant role in the inflammatory process. In acute inflammation, the endothelium regenerates to replace injured or dying endothelial cells, but new capillaries are not formed. In contrast, the principal vascular response in chronic inflammation is neovascularization. This is the type of inflammatory response that is elicited in juvenile rheumatoid arthritis, arteriosclerosis, and proliferative retinopathy. Chronic inflammation can also follow a surgical injury or the placement of a foreign object in the body, such as in the peritoneal cavity. These disease processes and wounding events potentiate the inflammatory response by activating inflammatory and endothelial cells in local and remote vascular compartments. Within the peritoneal cavity, adjacent visceral elements, such as the omentum and surrounding loops of bowel, become adherent to sites of early inflammation and fibrin matrix degradation to assist in tissue coverage and the delivery of additional inflammatory and cellular mediators of tissue repair.

There is minimal inflammation, fibroplasia or neovascularization in fetal tissue repair. This may be related to the fact that cytokine ratios and the extracellular matrix composition are altered. Fetal wounds are rich in hyaluronic acid, which persists in the wound for several weeks, throughout the course of healing. This is unlike the case for adult wounds in which the hyaluronic acid level peaks at three days, and decreases to zero in seven days. As fetal growth and differentiation nears completion at the end of gestation, hyaluronic acid levels decline, and wound healing takes on the characteristics of adult wound healing. The prolonged presence of hyaluronic acid in the matrix of fetal wounds is thought to promote fetal fibroblast movement and proliferation, while inhibiting cyto-differentiation. The modified hyaluronic acid composition of this invention may be biologically active, and thereby contribute to the reduction in the observed neovascularization experienced with its use.

The effect of hyaluronic acid on angiogenesis may depends on its molecular weight. High molecular weight hyaluronic acid is believed to inhibit blood vessel formation and be implicated in the differentiation and migration of many cell types. Conversely, low molecular weight hyaluronic acid, including degradation products of HA, such as oligosaccharides of 3 to 10 disaccharide units in length, may stimulate angiogenesis. HA oligosaccharides may act on endothelial cells in vitro, and stimulate cell proliferation and migration, two key elements associated with the formation of capillary sprouts.

Hyaluronic acid binds to certain cell surface receptors, such as CD44, RHAMM (Receptor for Hyaluronan Mediated Motility) and ICAM-1 (Intracellular Adhesion Molecule-1). CD44 is widely distributed throughout the body and is recognized as the major cell surface receptor for hyaluronic acid. HA-CD44 binding may be implicated in cell-cell and cell-substrate adhesion, cell migration, proliferation, and activation, as well as HA uptake and degradation. Its precise role in the peritoneum is unknown. The expression of RHAMM on cell surfaces is associated with cell locomotion. ICAM-1 is a cell adhesion molecule widely distributed on endothelial cells, macrophages, and other cells. The binding of HA to ICAM-1 is thought to influence endothelial cell-leukocyte binding, and thus to contribute to the control of ICAM-1 mediated inflammatory activation.

From the above description, one skilled in the art can easily ascertain the essential characteristics of the present invention, and without departing from the spirit and scope thereof, can make various changes and modifications of the invention to adapt it to various usages and conditions.

As one skilled in the art will appreciate, gels and films of the invention can be made using protocols that are within the method of the invention yet are different in particulars from those described here.

The following example is provided by way of illustration and is not intended to limit the invention except as set forth in the appended claims.

EXAMPLE

This example compares and contrasts the effects of Seprafilm and a control on the growth of vessels and the formation of adhesions.

88 C57BL6/J Nonagouti (black) mice, between 6 and 8 weeks old, weighing approximately 22 grams at the time of the procedure, were obtained, and a permanent black mark was used on their tails to identify the animals. Only healthy animals, previously unused in experimental procedures, were used in this experiment.

The animals were acclimated for a minimum of 24 hours prior to the experiment. Only animals that appeared normal (healthy appetite, bright clear eyes, no unusual exudate from any body orifice, alert and active posture) were subjected to the experimental procedure.

A maximum of 4 animals were housed in polycarbonate 7×11×5 inch cages. A maximum number of 10 animals were housed in each polycarbonate 10×19×6 inch large cage. The room temperature was maintained at 74° F. to 76° F. with 40% to 50% relative humidity, and a light/dark cycle of 12 hours/12 hours.

Food and tap water were provided ad libitum. Feed and water supplies may have had some contaminants, but that should not have had the potential to influence the outcome of the experiment. The experiment was performed in accordance with NIH guidelines as described in the Guide for the Care and Use of Laboratory Animals, National Academy Press (1996).

The mice were randomly separated to serve either as surgical controls (N=44 with n=16 in each group, except day 35, n=12), or receive Seprafilm (N=44 with n=16 in each group, except day 35, n=12). The mice were randomly assigned to be sacrificed on post-operative days 10, 15 and 35.

The mice were fasted for 6 hours prior to surgery. Sterile surgical procedures were performed using an operative Zeiss OPMI 7 microscope fitted with a 200-mm focal length lens. General anesthesia was provided with an isoflurane chamber. A rodent inhalation anesthesia machine was used. The individual animal was first placed in the chamber with an oxygen and isoflurane mixture (3L $O_2$ and 3L Isoflurane), then, upon induction, the animal was weighed and transferred to an animal mount, and connected to an anesthesia machine for continued anesthesia. The level of anesthesia was monitored by assessing the animal's vital signs, including heart rate, and spontaneous respiratory rate. The oxygen/isoflurane gas mixture flowed at approximately 1.5 L/min.

All four limbs of the animal were restrained with tape during surgery. The abdomen was shaved, cleansed with Betadine, and sterilely draped. An approximate 2.0-cm midline incision was made, and the abdominal wall everted so as to expose the left side of the peritoneal cavity. A 5 mm×5 mm×0.2 mm square piece of sterile polymeric silicone (Dow Corning Corporation, Medical Products, Midland, Mich., USA) was fixed posterior and lateral to the left epigastric artery and vein using two separate corner stitches of 8/0 Nylon. A cecal abrasion was created by stroking the anterior and posterior walls of the cecum 20 times each with sterile gauze. An adjacent peritoneal injury was created by clamping the sidewall of the peritoneal cavity for 30 seconds with a hemostat. Treatment animals underwent placement of three 1 $cm^2$ pieces of Seprafilm (Genzyme Corporation, Cambridge, Mass., USA) as follows: 1 piece was placed between the silastic patch and overlying bowel, 1 piece was wrapped around the cecum to cover the cecal abrasions, and 1 piece was placed on top of the bowel beneath the midline laparatomy incision. The peritoneal cavity was open for approximately 20 minutes per animal. The midline incision was closed with a single layer of interrupted 6/0 Nylon. A subcutaneous injection of 2 mg/kg of buprenorphine HCl (Buprenex™) was then given for management of postoperative pain.

The animals were allowed to recover, and their breathing pattern and state of alertness were observed by both the surgeon and assistant. Once the animal was fully awake, breathing in a normal pattern and ambulatory, it was returned to a new cage where food and drink were given ad libitum. During the postoperative period, the surgeon and assistant observed the mice daily, assessing each animal's breathing pattern, state of alertness, corneal clarity, food and liquid intake, as well as any signs of distress.

Both control and treatment animals were given subcutaneous injections of normal saline every other day for 10 days post surgery. There were a total of 88 animals, with n=16 in every group, except for day 35 with n=12. One animal from the day 35, Seprafilm group developed peritonitis, was euthanized and excluded from data analysis. All other animals are included in the results herein.

Animals from both groups were sacrificed on postoperative days 10, 15, and 35. Prior to sacrifice, the animals were weighed, shaved and their skin prepared with Betadine. The same method of anesthesia was used as above for the initial procedure. The abdomen was opened through a right paramedian incision, and the right side of the peritoneal cavity was swabbed for culture onto blood agar plates (Remel Microbiology), and incubated for 48 hours at 37° C. Both sides of the abdomen were carefully inspected for the presence of adhesions. The adhesions were scored based on extent, type and tenacity (see below). The abdominal wall and silastic patch were transilluminated, and photographs of the patch and any associated adhesions were taken with a 35 mm camera attached to the Zeiss microscope (see below). The patch was excised along with any associated adhesions, and preserved in 10% neutral buffered formalin. Spleen weights were taken at the time of sacrifice. Urine and serum samples were taken at sacrifice and stored at −80° C. and −20° C., respectively. Animals were then euthanized in a precharged $CO_2$ environment.

At the time of sacrifice the adhesions were assessed and scored. During sacrifice, the abdominal wall was everted and the silicone patch transilluminated using a custom-designed platform. This provided a clear image of the patch without light reflection for optimal imaging purposes. Photographs of the silastic patch and any associated adhesions were obtained using a 35 mm camera attached to the Zeiss microscope. A reticle was placed on the tissue adjacent to the patch. All measurements were standardized against the 0.1 mm grid of the reticle. Photographic slides of the images were digitized and analyzed using the computer UTHSCSA ImageTool program (developed at the University of Texas Health Science Center at San Antonio, Tex. and available from the Internet by anonymous FTP from maxrad6.uthscsa.edu).

The digitized images were used to calculate the percent of vascularized peritoneum over the patch. This was calculated by measuring the extent of vascularized peritoneum per area of patch not covered by an adhesion. If there was no adhesion present, the extent of vascularized peritoneum was measured per area of patch. The area under any associated adhesions was not considered in the calculation. This was done so as not to presume that vessels were present under the entire adhesion, nor to disturb the adhesions before histological analysis.

Adhesions were evaluated by carefully lifting the sides of the abdominal wall adjacent to where the silastic patch and cecal abrasions were located. The adhesions were scored using the classification contained in Bigatti, *Human Reproduction*, 10, pages 2290–2294, (1995), based on extent, type and tenacity, as shown in Table 1. The total adhesion score was calculated from the sum of the extent, type and tenacity scores for the adhesions to the silastic patch and cecal abrasion.

TABLE 1

| Characteristic | Adhesion Score |
|---|---|
| TENACITY | |
| None | 0 |
| Adhesions essentially fell apart | 1 |
| Adhesions lysed with traction | 2 |
| Adhesions required sharp dissection | 3 |
| TYPE | |
| None | 0 |
| Filmy, no vessels (transparent) | 1 |
| Dense, no vessels (translucent) | 2 |
| Dense, vascular, small vessels (diameter <50 µm) | 3 |
| Dense, vascular, large vessels (diameter 50–110 µm) | 4 |
| EXTENT | |
| (% of silastic patch surface covered by adhesions) | |
| 0 | 0 |
| <25 | 1 |
| 25–50 | 2 |
| 50–75 | 3 |
| >75 | 4 |

During the evaluation and scoring of adhesions, more than one visceral adhesion to the silastic patch in either the control or Seprafilm group was not detected. For example, in the day 10 control group, 10 of 12 adhesions were a single omental adhesion to the patch, 1 was a cecal adhesion, 1 was a bladder adhesion, and 4 animals had no adhesions, as shown in Table 2.

TABLE 2

|  | Day 10 | Day 15 | Day 35 |
|---|---|---|---|
| Control: | | | |
| Omentum | 10/16 | 15/16 | 9/12 |
| Other* | 2/16 | 0/16 | 1/12 |
| No Adhesions | 4/16 | 1/16 | 1/12 |
| Seprafilm: | | | |
| Omentum | 6/16 | 2/16 | 1/11 |
| Other* | 1/16 | 1/16 | 0/11 |
| No Adhesions | 9/16 | 13/16 | 11/11 |

*Other: Bladder, Bowel, Cecum or Liver

Adhesions associated with the cecal abrasions tended to be more complex and composed of multiple visceral elements, especially in the control animals, as shown in Table 3. In the Seprafilm cecal abrasion groups, the adhesions were less complex and commonly composed of multiple visceral elements.

TABLE 3

|  | Day 10 | Day 15 | Day 35 |
|---|---|---|---|
| Control: | | | |
| Omentum | 6/16 | 4/16 | 10/12 |
| Peritoneal Sidewall | 2/16 | 1/16 | 0/12 |
| Other* | 6/16 | 12/16 | 9/12 |
| No Adhesions | 8/16 | 8/16 | 2/12 |
| Seprafilm: | | | |
| Omentum | 11/16 | 10/16 | 7/11 |
| Peritoneal Sidewall | 0/16 | 0/16 | 0/11 |
| Other | 3/16 | 2/16 | 3/11 |
| No Adhesions | 5/16 | 6/16 | 2/11 |

*Other: Bladder, Bowel, Mesentery, Cecum, Silastic Patch or Button.

The patch adhesion scores were obtained by summing the extent, type and tenacity scores. On average, the total adhesion score was essentially a measure of the extent of adhesion formation since the majority (90%) of the adhesions required sharp dissection (tenacity=3). These adhesions also had dense, vascular, large vessels (type=4). As a result, adhesion scores varied as the extent of the adhesion coverage over the patch varied. In control animals, the average total adhesion scores were 6.6 at day 10 (SE=1.2, n=16), 8.8 at day 15 (SE=0.7, n=16), and 8.3 at day 35 (SE=1.1, n=16). In the Seprafilm animals, the average total adhesion scores were significantly less compared with the control animals and decreased over time. The total adhesion scores for the Seprafilm animals were 3.5 at day 10 (SE=1.1, n=16), 1.1 at day 15 (SE=0.6, n=16), and 1.0 at day 35 (SE=1.0, n=11). This is shown graphically in FIG. 1.

Figure 2:
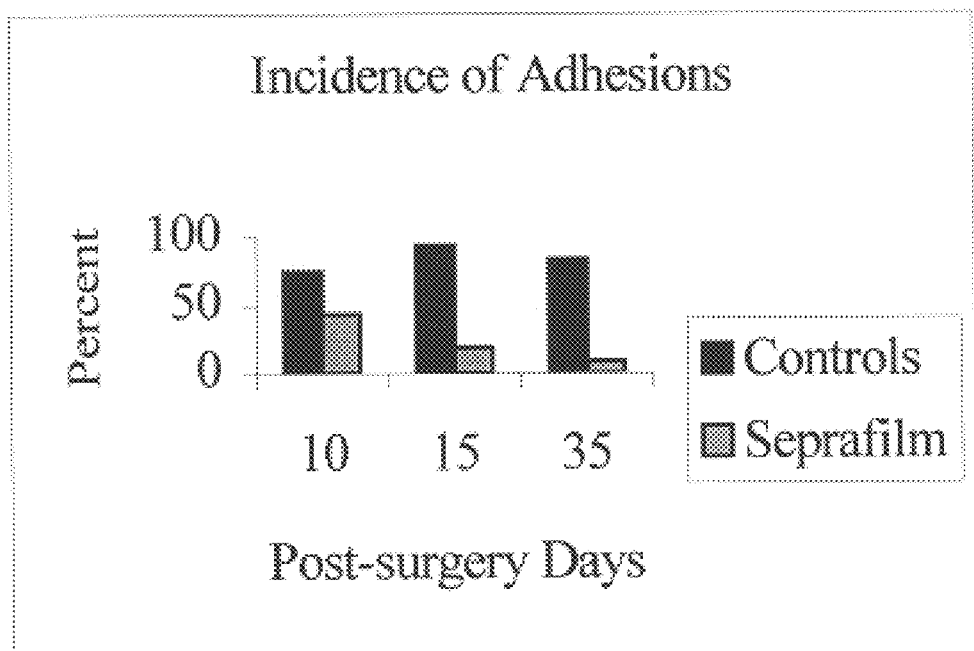
FIG. 2 is a bar graph illustrating the incidence of adhesions for Seprafilm treated and control animals at 10, 15 and 35 days following surgery.

The frequency of adhesion formation in control and treatment animals is summarized in Table 4 and represented graphically in FIG. 2. In control animals, the incidence of adhesions was 75% at day 10 (n=16), 94% at day 15 (n=16), and 83% at day 35 (n=12). In Seprafilm animals, the incidence of adhesions decreased over time, from 44% at day 10 (n=16), to 19% at day 14 (n=16), and 9% at day 35 (n=11). The incidence of adhesion formation in the treated animals was significantly less when compared to the control animals at day 15, p<0.001, and at day 35, p=0.001.

TABLE 4

| Total N* | # of animals lost from analysis** | Day 10 | Day 15 | Day 35 |
|---|---|---|---|---|
| 44 | 0 | 12/16 | 15/16 | 10/12 |
| 44 | 1 | 7/16 | 3/16 | 1/11 |
| | | | p < 0.001 | p = .001 | n = 16 in each group except day 35 n = 12 is; animal euthanized s, n = 16 in each group except day 35, n = 11

Figure 3:
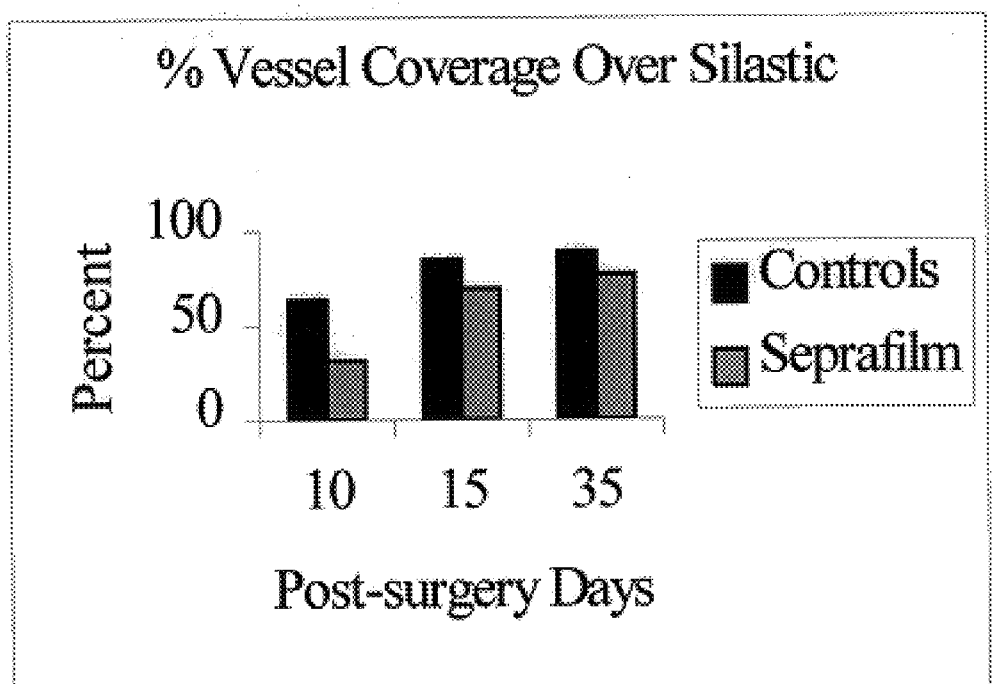
FIG. 3 is a bar graph illustrating the area of vessel coverage over a silastic patch for Seprafilm treated and control animals at 10, 15 and 35 days following surgery.

Angiogenesis was evaluated by measuring the area of vascularized peritoneum over the silastic patch in control and Seprafilm animals at days 10, 15 and 35, as shown graphically in FIG. 3. In the day 10 Seprafilm animals, vascular ingrowth over the patch was significantly less than in day 10 control animals (32%, SE=7.1, n=16 versus 64%, SE=8.9, n=16, p=0.02). Thereafter, there was rapid vessel ingrowth over the patch in the Seprafilm animals, such that on days 15 and 35, there was no significant difference in vessel coverage over the patch.

To discern whether vessel ingrowth over the patch in day 10 control and Seprafilm animals may be influenced by the presence or absence of adhesions, we further stratified the day 10 animals, as shown in Table 5. In the groups without adhesions, there was less vascular coverage in the Seprafilm treated animals, suggesting that Seprafilm delayed vessel ingrowth over the silastic patch. When we looked at those animals with adhesions, the percent vascular coverage was again less in the Seprafilm animals compared with the control group. Because of the small sample sizes, it is not possible to ascribe the inhibition of vessel coverage over the silastic patch in the day 10 Seprafilm animals to a direct anti-angiogenic or pure barrier effect. Instead, our results suggest that Seprafilm has a dual effect, with perhaps the barrier effect being greater than the inhibitory effect on endothelial cell growth.

TABLE 5

|  | All Animals (N = 32) | Animals with Adhesions (N = 19) | Animals without Adhesions (N = 13) |
|---|---|---|---|
| Control | 64% (n = 16) | 74% (n = 12) | 31% (n = 4) |
| Seprafilm | 32% (n = 16) | 43% (n = 7) | 23% (n = 9) |
| p-value | p = .02 | p = .091 | p = 0.6993 |

What is claimed is:

1. A method for inhibiting angiogenesis in a mammal comprising locally administering to the site of tumor formation in said mammal an angiogenesis inhibiting amount of a pharmaceutical preparation comprising the reaction product of hyaluronic acid, carboxymethylcellulose, and a carbodiimide.

2. The method of claim 1 wherein the pharmaceutical preparation is in the form of a film.

3. The method of claim 1 wherein the pharmaceutical preparation is in the form of a gel.

* * * * *